United States Patent [19]

Park

[11] 4,394,233

[45] Jul. 19, 1983

[54] PROCESS FOR PREPARING ETHYL α-CHLOROETHYL CARBONATE

[75] Inventor: Sang-Woo Park, Seoul, Rep. of Korea

[73] Assignee: The Korea Advanced Institute of Science and Technology, Seoul, Rep. of Korea

[21] Appl. No.: 287,641

[22] Filed: Jul. 28, 1981

[30] Foreign Application Priority Data

Dec. 23, 1980 [KR] Rep. of Korea .................... 4891/80

[51] Int. Cl.$^3$ ............................................. B01J 19/12
[52] U.S. Cl. ............................................. 204/158 HA
[58] Field of Search ................................. 204/158 HA

[56] References Cited

U.S. PATENT DOCUMENTS 2,918,478  12/1959  Newman .................... 204/158 HA
3,454,597  7/1969   Tong et al. ................. 204/158 HA Primary Examiner—Howard S. Williams
Attorney, Agent, or Firm—Holman & Stern

[57] ABSTRACT

Diethylcarbonate is chlorinated with dry chlorine gas in the presence of ultraviolet rays to give ethyl α-chloroethyl carbonate in a good yield. The chlorination is preferably carried out, with or without a carbon tetrachloride solvent as a reaction medium, at a range of temperature of 45° to 55° C.

5 Claims, No Drawings

PROCESS FOR PREPARING ETHYL α-CHLOROETHYL CARBONATE

FIELD OF THE INVENTION

This invention relates to a novel process for preparing ethyl α-chloroethyl having the formula:

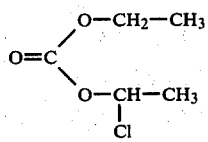

It has been known that the above compound reacts with the carboxylic group of penicillins and cephalosporins which are antibiotics in the β-lactam series, to form an ester which increases the absorptive power of oral preparations and is useful in enhancing the potency of those preparations.

BACKGROUND OF THE INVENTION

Hitherto, only one method has been proposed for preparing ethyl α-chloroethyl carbonate-chloro-diethylcarbonate. See, H. Müller, Annalen der Chemie, 258, 50 (1890). In this method, the desired compound, which is exactly identical with Compound I mentioned above, was prepared by chlorinating ethyl-chloroformate having the formula:

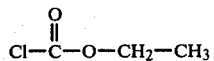

under the irradiation of sunlight and then reacting the resulting compound, α-chloroethyl chloroformate having the formula:

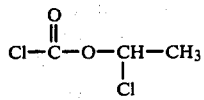

with ethanol, according to the following reaction:

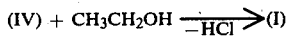

In this prior art, however, the yield of Compound IV resulting from chlorination under sunlight was very poor (less than 20%) and furthermore, undesirable side-reactions occurred markedly. Therefore, it was not possible to isolate only the pure α-chloroethyl chloroformate of Formula IV from the mixture of the resulting by-products. According to the conventional prior art, in fact, it was disclosed that five separate by-products beside Compound IV would be produced; however the extent of the yield of the chief product, Compound IV, was not mentioned therein. It merely pointed out that the production of dichlorinated compound, which is one of the five by-products, was remarkably higher. Expecially problematic, in the process for chlorinating Compound III, is the necessity for the presence of sunlight in preparing Compound IV, which may hinder industrial processing methods.

The utility of the compound prepared according to the invention, has been disclosed in various prior patents, such as U.S. Pat. Nos. 3,873,521 (Mar. 25, 1975) and 3,939,270 (Feb. 17, 1976), and Japanese Laid-Open Patent Publication No. (Sho) 48-8,796 (Feb. 3, 1973); however, no alternative proposal has been advanced concerning a method for preparing the compound itself since the H. Müller process was presented.

BRIEF SUMMARY OF THE INVENTION

Therefore, the inventor has long studied processes for preparing ethyl α-chloroethyl carbonate, which are industrially acceptable and have generally eliminated the problems associated with the conventional prior art method. The inventor has thus found that the direct chlorination of diethylcarbonate under the irradiation of ultraviolet rays with a certain wave-length can, in a convenient and simple manner, produce Compound I in a good yield.

In summary, the process, according to the invention, is featured by chlorinating diethylcarbonate having the formula:

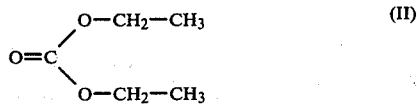

with dry chlorine gas under the irradiation of ultraviolet rays to afford the desired Compound I. The chlorination is preferably achieved in a carbon tetrachloride solvent as a reaction medium; however, the presence of the solvent is not essentially required.

In the present invention, the chlorine gas is passed into the solution of Compound II under the irradiation of ultraviolet rays and therefore, the process for obtaining Compound I can be simplified. In such chlorination, it is necessary to use, as a starting material, diethylcarbonate having a very high purity. The purity of diethylcarbonate for use in industrial purposes is lower and therefore, it should be treated first with calcium chloride and then purified by means of fractional distillation so that the yield of the desired compound therefrom is increased. The important factors for a chlorination reaction include the selection of the range of appropriate reaction temperatures and times, the amount of chlorine gas introduced to the reaction system, and the kind of reaction medium. For instance, in the case of a reaction temperature of about 0° C., the reaction will occur in a lower yield (about 7%), as well as, in the case of a reaction temperature of 80° C. or higher, since two or more chlorine atoms readily react with ethyl group to produce dichlorides, the reaction activity will also be decreased.

In the present invention, it has been found that the proper reaction temperature ranges from 45° C. to 55° C. and the reaction time, within the range of this temperature, requires about five hours. Under identical reaction conditions, if the reaction time is shortened, a decreased yield results. In order to obtain a desirable result therefore, it is preferable to use chlorine gas in the ratio of 1.2 to 1.4 moles to 1 mole of diethylcarbonate as the starting material.

According to the invention, it is possible to increase the yield of the final product by 10% or more by carrying out the reaction by adding the carbon tetrachloride solution as a reaction medium to the diethylcarbonate solution, rather than by directly passing dry chlorine gas into the diethylcarbonate solution. For such chlorination, a 1 L. flask (Ace-Hanovia) equipped with a 100 watt mercury lamp and a gas inlet tube is preferred.

The process of the invention, can be summarized by means of the following reaction:

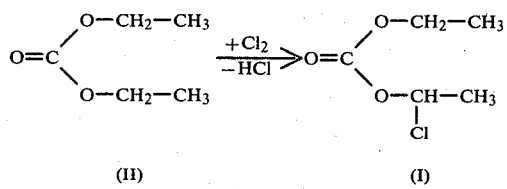

PREFERRED EMBODIMENTS OF THE INVENTION

The following specific description is given to enable those skilled in the art to more clearly understand and practice the present invention. It should not be considered to be a limitation upon the true scope of the invention, but merely to be illustrative and representative thereof. It should be noted that in the following examples, the yield was calculated to the exclusion of the amount of the unreacted diethylcarbonate.

EXAMPLE 1

Into a 1 L. flask equipped with a 100 watt mercury lamp (wave-length of ultraviolet ray: 185-350 nm) and a gas inlet tube, 236.6 grams (2 moles) of pure diethylcarbonate were placed and then the flask was cooled, so that the contents of the flask could be maintained at $-3°$ to $0°$ C. Maintaining the temperature with this range the reactant was irradiated with ultraviolet rays, and, at that time, chlorine and nitrogen gases were introduced into the flask through the gas inlet tube. The flask was occasionally cooled, so that its contents could be maintained within the above described temperature range. Two moles (44,800 ml) of chlorine gas and any added nitrogen gas were passed consistently into the flask over a period of five hours, and thereafter the introduction of chlorine gas was terminated and the residual chlorine and hydrogen chloride gases were expelled completely from the reaction mixture by purging with nitrogen gas. Then, a fractional distillation tube was connected to the flask to distill unreacted diethylcarbonate, resulting in 24 grams of the desired product, ethyl α-chloroethyl carbonate. B.P.: 160°-163° C.; Yield: 7.2% to the consumed diethylcarbonate; IR (Neat) (cm$^{-1}$); 2950; 1740; 1430; 1360; 1330; 1250; 1100; 1000; 900; 850; 780; NMR (CCl$_4$) (δ=ppm): 6.32 (q, 1H); 4.22 (q, 2H); 1.8 (d, 3H); 1.3 (t, 3H).

EXAMPLE 2

The procedure of Example 1 was repeated, except that the temperature of the contents of the flask was maintained at 20° C. to obtain 34 grams of ethyl α-chloroethyl carbonate. B.P.: 160°-163° C.; Yield 13.5% to the consumed diethylcarbonate. The data of the IR and the NMR were identified to be the same as those in Example 1.

EXAMPLE 3

The procedure of Example 1 was repeated, except that the temperature of the contents of the flask was maintained at 40° C. to obtain 66 grams of ethyl α-chloroethyl carbonate. B.P.: 160°-163° C.; Yield: 53.5% to the consumed diethylcarbonate. The data of the IR and the NMR were identified to be the same as those in Example 1.

EXAMPLE 4

The procedure of Example 1 was repeated, except that the reaction temperature was changed to 80° C. to yield 118 grams of ethyl α-chloroethyl carbonate. B.P.: 160°-163° C.; Yield: 53.5% to the consumed diethylcarbonate. The data of the IR and the NMR were identified to be the same as those in Example 1.

EXAMPLE 5

The procedure of Example 1 was repeated, except that the reaction temperature was maintained at a range of 50° C. to 52° C. to give 121.2 grams of ethyl α-chloroethyl carbonate. B.P.: 160°-163° C.: Yield: 57.3% to the consumed diethylcarbonate. The data of the IR and the NMR were identifiled to be the same as those in Example 1.

EXAMPLE 6

Into the same flask as used in Example 1, 236.6 grams (2 moles) of pure diethylcarbonate were added, and then 2.6 moles of chlorine gas were introduced into the flask over a five hour period at a range of 50° C. to 52° C. under the irradiation of ultraviolet rays. When the reaction was completed, the unreacted diethylcarbonate was removed by subjecting it to fractional distillation to yield 131 grams of ethyl α-chloroethyl carbonate. B.P.: 160°-163° C.; Yield: 59.8% to the consumed diethylcarbonate. The data of the IR and the NMR were identified to be the same as those in Example 1.

EXAMPLE 7

The procedure of Example 6 was repeated, except that the diethylcarbonate was mixed with 40 ml (0.29 mole) of carbon tetrachloride, using the same conditions, to afford 146 grams of alpha-chloro-diethylcarbonate. B.P.: 160°-163° C.; Yield: 71.6% to the amount of the diethylcarbonate used to complete the reaction. The data of the IR and the NMR were also identified to be the same as those in Example 1 above.

What is claimed is:

1. A process for preparing ethyl α-chloroethyl carbonate having the formula:

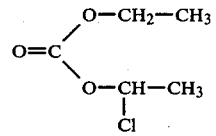

which comprises chlorinating diethylcarbonate having the formula:

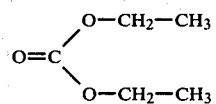

with chlorine gas in the presence of ultraviolet radiation.

2. The process according to claim 1, wherein the reaction temperature ranges from 45° C. to 55° C.

3. The process according to claim 1, wherein the amount of chlorine gas used is 1.2 to 1.4 moles per mole of diethylcarbonate employed as a starting material.

4. The process according to claim 1, wherein carbon tetrachloride is employed as a reaction medium during chlorination.

5. A process for preparing ethyl α-chloroethyl carbonate, comprising chlorinating diethylcarbonate with 1.2 to 1.4 moles of chlorine gas per mole of diethylcarbonate in a carbon tetrachloride reaction medium maintained at a temperature in the range of 45° C. to 55° C. in the presence of ultraviolet radiation.

* * * * *